United States Patent [19]

Imran

[11] Patent Number: 5,626,593

[45] Date of Patent: *May 6, 1997

[54] FLEXIBLE ELONGATE DEVICE HAVING A DISTAL EXTREMITY WITH A VIBRATORY IMPACT TIP AND METHOD

[75] Inventor: Mir A. Imran, Palo Alto, Calif.

[73] Assignee: Intella Interventional Systems, Sunnyvale, Calif.

[*] Notice: The term of this patent shall not extend beyond the expiration date of Pat. No. 5,449,369.

[21] Appl. No.: 444,311

[22] Filed: May 18, 1995

Related U.S. Application Data

[63] Continuation of Ser. No. 235,127, Apr. 28, 1994, Pat. No. 5,449,369, which is a continuation of Ser. No. 983,837, Dec. 1, 1992, abandoned.

[51] Int. Cl.⁶ .................................................. A61B 17/22
[52] U.S. Cl. ..................... 606/159; 606/169; 606/171
[58] Field of Search .................................. 128/656–658, 128/772, 898; 604/22, 95–104, 280–282; 606/1, 128, 159, 167, 170, 171, 169, 190–194

[56] References Cited

U.S. PATENT DOCUMENTS

| | | | |
|---|---|---|---|
| 4,870,953 | 10/1989 | Michael et al. | 606/159 |
| 4,926,858 | 5/1990 | Gifford et al. | 606/159 |
| 4,944,727 | 7/1990 | McCoy . | |
| 4,964,409 | 10/1990 | Tremulis . | |
| 4,979,939 | 12/1990 | Shiber | 606/170 |
| 5,041,082 | 8/1991 | Shiber | 604/22 |
| 5,114,402 | 5/1992 | McCoy | 604/95 |
| 5,116,350 | 5/1992 | Stevens | 606/171 |
| 5,120,308 | 6/1992 | Hess | 604/95 |
| 5,127,917 | 7/1992 | Niederhauser et al. | 606/159 |
| 5,158,564 | 10/1992 | Schnepp-Pesch et al. . | |
| 5,234,451 | 8/1993 | Osypka | 606/159 |
| 5,243,997 | 9/1993 | Uflacker et al. | 128/772 |
| 5,246,447 | 9/1993 | Rosen et al. | 606/178 |
| 5,267,954 | 12/1993 | Nita | 606/159 |
| 5,449,369 | 9/1995 | Imran | 606/159 |

FOREIGN PATENT DOCUMENTS

WO9111213  8/1991  WIPO .

OTHER PUBLICATIONS

Dretler et al, Conversion of the Electrohydraulic Electrode to an Electromechanical Stone Impactor: Basic Studies and a Case Report; The Journal of Urology, vol. 146, pp. 746–750, Sep. 1991.

Primary Examiner—Glenn Dawson
Attorney, Agent, or Firm—Flehr, Hohbach, Test, Albritton & Herbert

[57] ABSTRACT

A flexible elongate device including a flexible elongate tubular member having proximal and distal extremities. A flexible coil spring is provided having proximal and distal extremities. The proximal extremity of the coil spring is secured to the distal extremity of the flexible elongate tubular member. A rounded tip is secured to the distal extremity of the coil spring. A flexible elongate element having proximal and distal extremities is disposed within said coil spring and extends longitudinally of the coil spring. The distal extremity of the flexible elongate element is secured to the rounded tip. A vibrator is secured to the proximal extremity of the flexible elongate element for imparting vibratory motion to the flexible elongate element to cause vibratory impact motion of the rounded tip in a direction longitudinal of the axis of the flexible elongate element.

14 Claims, 1 Drawing Sheet

FLEXIBLE ELONGATE DEVICE HAVING A DISTAL EXTREMITY WITH A VIBRATORY IMPACT TIP AND METHOD

This is a continuation of application Ser. No. 08/235,127 filed Apr. 28, 1994, now U.S. Pat. No. 5,449,369, which is a continuation of Ser. No. 07/983,837 filed Dec. 1, 1992, now abandoned.

BACKGROUND OF THE INVENTION

This invention relates to a flexible elongate device having a distal extremity with a vibratory impact tip and method particularly useful for catheters and guide wires.

In certain medical procedures, as for example in angioplasty procedures, lesions or stenoses have been encountered in vessels which are difficult to cross because they totally or almost totally occlude the vessel. Thus, there is a need for a device which will make it possible to penetrate and to cross such stenoses or lesions.

SUMMARY OF THE INVENTION

In general, it is an object of the present invention to provide a flexible elongate device having a distal extremity with a vibratory tip and a method which can be utilized for penetrating and crossing stenoses or lesions which occlude vessels in a patient.

Another object of the invention is to provide a device and method of the above character which can be utilized with a distal extremity which is flexible and which can be adjusted in stiffness.

Another object of the invention is to provide a device and method of the above character in which distal extremity follows the path of least resistance.

Another object of the invention is to provide a device and method of the above character which will not perforate the vessel wall.

Another object of the invention is to provide a device and method of the above character in which the distal extremity can be steered.

Another object of the invention is to provide a device and method of the above character which can be utilized with catheters and/or guide wires.

Another object of the invention is to provide a device and method which is particularly useful in crossing hard-to-penetrate lesions or stenoses.

Additional objects and features of the invention will appear from the following description in which the preferred embodiments are set forth in detail in conjunction with the accompanying drawings.

DETAILED DESCRIPTION OF THE PREFERRED EMBODIMENTS

In general, the flexible elongate device incorporating the present invention consists of a flexible tubular member having proximal and distal extremities. A flexible coil spring is provided which has proximal and distal extremities. Means is provided for securing the proximal extremity of the coil spring to the distal extremity of the flexible elongate tubular member. A rounded tip is secured to the distal extremity of the coil spring. A flexible elongate element having proximal and distal extremities is disposed within the coil spring and extends longitudinally of the coil spring. Means is provided for securing the distal extremity of the flexible elongate element to the rounded tip. Means is secured to the proximal extremity of the flexible elongate element for imparting vibratory motion to the flexible elongate element to cause vibratory motion of the rounded tip in a direction parallel to the longitudinal axis of the flexible elongate element.

Figure 1:
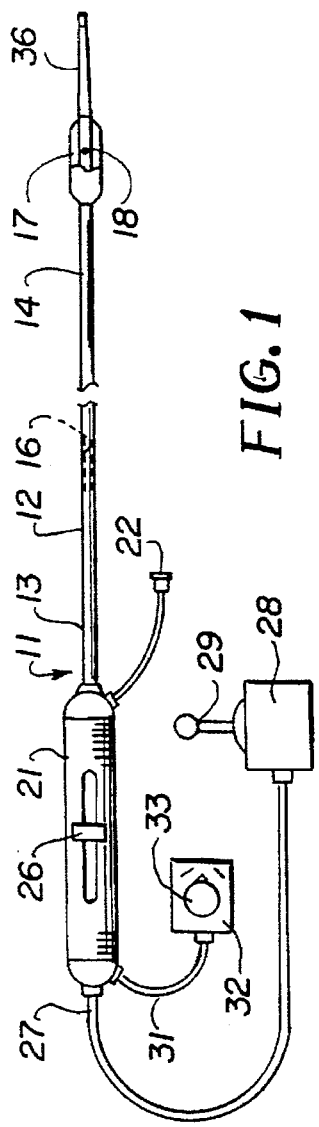
FIG. 1 is a side elevational view of a device incorporating the present invention in the form of a balloon dilatation catheter.

More in particular as shown in FIG. 1, the device of the present invention takes the form of a balloon dilatation catheter 11 which consists of a flexible elongate member 12 having proximal and distal extremities 13 and 14 and a lumen 16 extending from the proximal to the distal extremity an inflatable balloon 17 is mounted on the distal extremity 14. A hole 18 is provided in the flexible elongate member 12 which establishes communication between the interior of the balloon 17 and the lumen 16. A control mechanism 21 is mounted on the proximal extremity 13. The control mechanism 21 is provided with a tube 22 which is in communication with the lumen 16 so that a fluid can be supplied to the lumen for inflating and deflating the balloon 17.

The flexible elongate member 12 and the control mechanism 21 are substantially the same as described in the co-pending application, Ser. No. 07/983,899, filed Dec. 1, 1992. As disclosed therein, the control mechanism 21 includes a linear potentiometer (not shown), the slider of which is controlled by a control, member 26 which is movable longitudinally of the control mechanism. A cable 27 extends from the control mechanism 21 and is connected to a joystick control 28 which includes a joystick 29 for controlling the movement of the distal extremity of the balloon dilatation catheter 11 as hereinafter described. Another cable 31 connected to the control mechanism 21 is connected to a power supply 32. The power supply 32 is provided with a control knob 33 for a rheostat (not shown) provided within the power supply 32.

The balloon dilatation catheter is provided with a distal extremity in the form of a coil spring assembly 36, the details of which will hereinafter be described.

Figure 2:
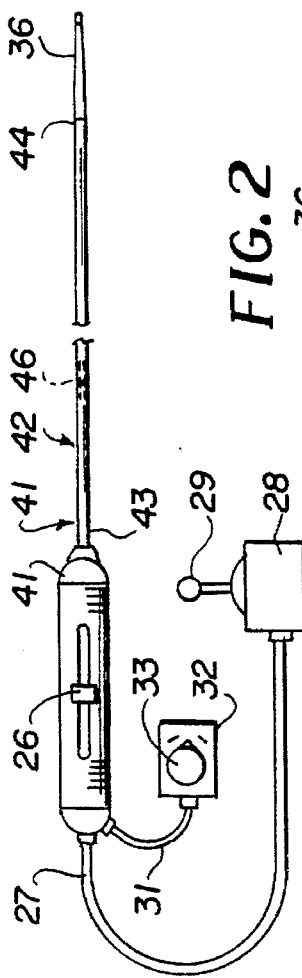
FIG. 2 is a side elevational view of a device incorporating the present invention in the form of a guide wire.

Another embodiment of the device of the present invention is shown in FIG. 2 which takes the form of guide wire 41. The guide wire 41 consists of a flexible elongate member 42 having proximal and distal extremities 43 and 44 and having a bore 46 extending from the proximal extremity 43 to the distal extremity 44. The flexible elongate member 42 is formed of a suitable material such as a stainless steel tube as described in co-pending application, Ser. No. 07/983,899, filed Dec. 1, 1992, now abandoned.

A control mechanism 41 substantially identical to the control mechanism 21 is mounted on the proximal extremity 43 and differs from the control assembly 21 by the omission of the tube 22. The distal extremity of the guide wire 41 carries a coil spring assembly 36 of the same type as carried by the distal extremity of the balloon dilatation catheter 11. The coil spring assembly 36 is secured to the distal extremity 14 of the flexible elongate member 12 or the distal extremity 44 of the flexible elongate member 42 by suitable means such as an epoxy in the case of adhering the same to a plastic tubular member 12 for a catheter or by welding 51 in the event of a stainless steel hypotube 42 for the guide wire.

Figure 3:
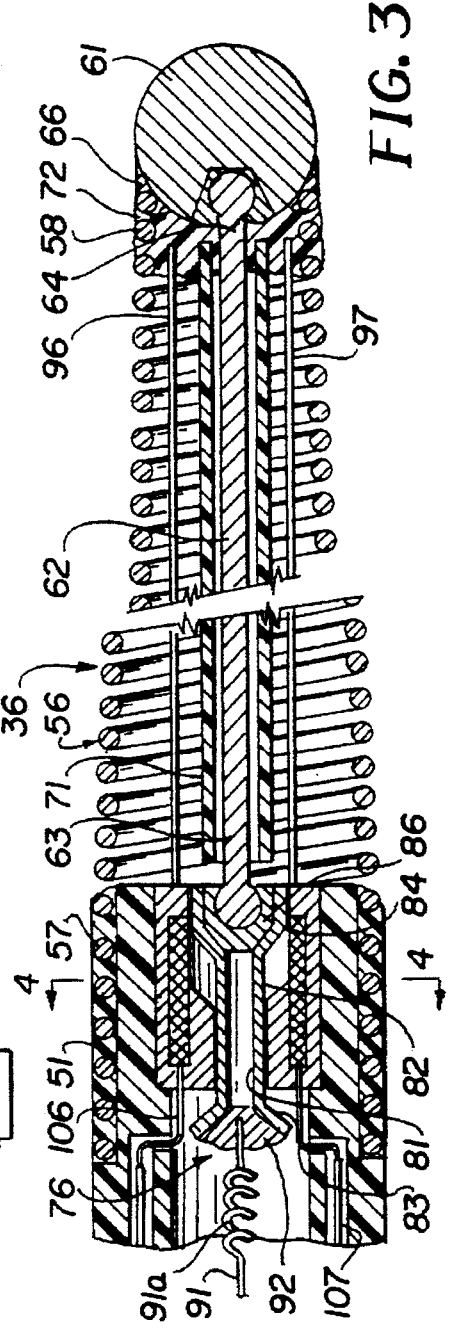
FIG. 3 is a greatly enlarged cross-sectional view of the distal extremity of the devices shown in FIGS. 1 and 2.

The coil spring assembly 36 consists of an elongate tapered coil spring 56 having proximal and distal extremities 57 and 58. The coil spring 56 is formed of a suitable radiopaque material such as a platinum-tungsten alloy or palladium. The coil spring 56 can be of a suitable diameter, as for example for a guide wire tapering from an outer diameter of 0.014" to 0.008" and for a catheter commencing with an outside diameter of 0.35" to a minimum diameter at the distal extremity of 0.015". The proximal extremity 57 is secured to the flexible elongate member 12 of the flexible elongate member 42 in the manner hereinbefore described. A rounded tip 61 is provided as a part of the coil spring assembly 36 and also is formed of a suitable radiopaque material such as gold or stainless steel. Means is provided for securing the rounded tip 61 to the coil spring assembly 61 and consists of a flexible elongate element which is disposed within the interior of the tapered coil spring 56 and extends longitudinally thereof. The flexible elongate element 62 is provided with proximal and distal extremities 63 and 64. The flexible elongate element 62 can be formed of a suitable material such as stainless steel. Alternatively, it can be formed of a shape-memory alloy element. The distal extremity 64 is bonded to the rounded tip 61 as shown in FIG. 3. Alternatively it can be soldered to tip. In addition, the rounded tip 61 is secured to the distal extremity 58 of the tapered coil spring 56 by suitable means such as solder 66.

In order to permit reciprocatory movement of the flexible elongate element 62 in a direction substantially parallel to the longitudinal axis and to minimize frictional engagement with the flexible elongate element 62 during such movement, the flexible elongate element 62 is slidably mounted within a tube 71 formed of a suitable material such as a flexible plastic such as polyethylene. By way of example, the flexible elongate element 62 can have a suitable diameter, as for example 0.005"–0.008" and is disposed within a tube 71 having an inside diameter of 0.009" and having a wall thickness of 0.001". The tube 71 extends substantially the entire length of the tapered coil spring 56 and has its distal extremity secured within the distal extremity of the coil spring 58 by suitable means such as an epoxy 72.

Figure 4:
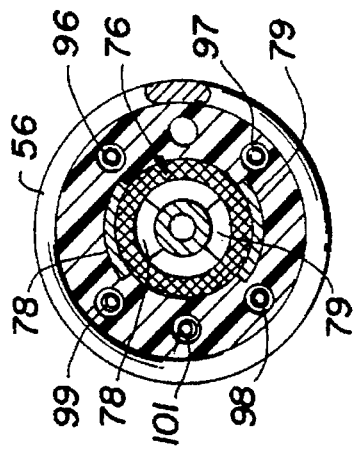
FIG. 4 is a cross-sectional view taken along the line 4—4 of FIG. 3.

Means is provided for imparting vibratory reciprocatory movement of the flexible elongate member 62 in the form of a solenoid 76. The solenoid 76 consists of a cylindrical coil 77 formed of conducting wire and segmented pole pieces 78 and 79 which are wrapped around the coil winding 77 as shown particularly in FIGS. 3 and 4. The solenoid 76 is provided with a bore 81 through which a plunger 82 formed of a suitable magnetic material such as steel extends. The plunger 82 is provided with an outwardly swaged proximal end 83 and outwardly swaged distal end 84 as shown particularly in FIG. 3. Means is provided for bonding the proximal extremity 63 of the flexible elongate element 62 into the swaged end 84 of the plunger 82 such as by the use solder 86. The proximal swaged end 83 of the plunger 82 is swaged to provide a stop to prevent the plunger from passing out of the bore 81. In this manner, the plunger 82 in conjunction with the flexible elongate element 62 serves as a safety ribbon or element for the rounded tip 61 to prevent it from separating from the distal extremity of the tapered coil spring 56.

In the event that the flexible elongate element 62 is in the form of a shape-memory alloy element, it is necessary to supply electrical energy to that element. This can be accomplished by use of an insulated conductor 91 connected to the proximal extremity 83 of the plunger 82 by suitable means such as solder 92 so that the plunger 82 can serve as a conductor leading to the shape-memory alloy element 62. The conductor 91 can be provided with a strain relief coiled portion 91a to permit the plunger 82 to reciprocate within the solenoid 76.

Since it is desirable that the distal extremity of the catheter 11 or of the guide wire 41 be steerable, four circumferentially spaced-apart elements 96, 97, 98 and 99 have been provided which have a negative coefficient of expansion and extend interiorally of the tapered coil spring 56. Their distal extremities are secured in the epoxy 72 and are electrically connected to an insulated return conductor 101. The elements 96–99 are connected to conductors (not shown) which extend to the proximal extremity of the flexible elongate member 12 or the flexible elongate member 42 and are connected through the cable 27 to the joystick control 28. The return conductor 101 also extends to the proximal extremity of the flexible elongate members 12 or 42 and is connected through the cable 27 to the joystick control 28. In this manner, the distal extremity of the catheter 11 or the guide wire 41 can be controlled in the manner described in co-pending application, Ser. No. 07/983,899, filed Dec. 1, 1992, now abandoned.

A pair of additional conductors 106 and 107 are connected to the solenoid coil 77 and extend from the distal extremities 14 or 44 of the flexible elongate members 12 or 42, respectively, to the proximal extremities 13 and 43 of the same and extend through the control mechanism 21 and are connected into the cable 31 connected to the power supply 32. The power supply includes a rheostat (not shown) which is controlled by a knob 33 which controls the amount of current which is supplied to the solenoid to thereby adjust the magnetic forces applied to the plunger.

Operation and use of the device with a vibratory impact tip may now be briefly described in conjunction with the method of the present invention. Let it be assumed that the catheter 11 or the guide wire 41 has been introduced into a vessel of the patient, as for example through the femoral artery of the patient and that the distal extremity has been advanced into a coronary artery by steering the same by the use of the joystick 29 on the joystick control 28. Let it be assumed that the distal extremity 36 has been advanced so that it has reached a stenosis in the vessel which it is unable to cross. At this time, the cardiologist can operate the control knob 33 to turn on the vibrator in the form of the solenoid 76 to supply current through the conductors 106 and 107 to the coil 77 in an interrupted manner by use of conventional circuitry such as a switching transistor driven by a square wave oscillator to cause reciprocatory motion against the yieldable force of the coil spring 56. Thus, there is created a high frequency vibration ranging from 10 Hz to 100 KHz which is applied to the tip 61 to cause the tip to penetrate the stenosis in the vessel. The rounded tip will cause the tip to follow the path of least resistance through the stenosis rather than through the vessel wall because it is normally disposed at right angles to the direction of longitudinal vibration of the tip 61. The amplitude of the vibrations can be increased or decreased depending upon the positioning of the control knob 33. In this manner, it should be possible for the tip 61 of the coil spring assembly 36 to penetrate the most difficult lesion or stenosis and to cross the same. After this has been accomplished with a guide wire 41, a balloon dilatation catheter of a conventional type can be inserted over the guide wire 41 and introduced through the stenosis so that the balloon is in alignment with the stenosis. The balloon 17 can be inflated for dilating the stenosis like in a conventional angioplasty procedure. After the appropriate dilation has been accomplished, the balloon dilatation catheter and the guide wire 41 can be removed.

If a balloon dilatation catheter 11 having a coil spring assembly 36 forming the distal extremity thereof is utilized, the catheter 11 can be inserted without the use of the guide wire and advanced to the stenosis by use of the joystick control 28, after which the control knob 33 can be operated to cause vibratory impact motion of the tip 61 to occur to cause the tip 61 to cross the stenosis or lesion in the vessel and to permit the catheter 11 to thereafter be advanced to bring the balloon 17 into alignment with the stenosis. After the balloon is in the proper position, it can be inflated and deflated by introducing a fluid into the tube 22 in a conventional manner.

It should be appreciated that when the flexible elongate element 62 is in the form of a shape-memory alloy element, the stiffness of it can be increased to ensure that the reciprocatory forces generated by the solenoid 76 are transmitted to the tip 61. This can be accomplished by moving the control member 26 to advance the slider to cause additional current to be supplied through the shape-memory alloy element 62 to stiffen the same as its temperature is increased.

It is apparent from the foregoing that there has been provided a flexible elongate device which has a distal extremity with a vibrating impact tip which can be utilized to penetrate and across difficult lesions or stenoses in a vessel of a patient. This is particularly important because it reduces the possibility of the patient having to undergo bypass surgery.

What is claimed is:

1. A flexible elongate device for crossing a stenosis of a totally or almost totally occluded vessel of a patient, comprising a flexible elongate tubular member having proximal and distal extremities, a rounded tip, electrically actuatable means carried by the distal extremity of the flexible elongate tubular member, means for connecting the electrically actuatable means to the rounded tip and means for supplying electrical energy from the proximal extremity of the flexible elongate tubular member to the electrically actuatable means at the distal extremity of the flexible elongate tubular member for imparting vibratory impact motion to the rounded tip for facilitating advancement of the rounded tip through the stenosis.

2. A device as in claim 1 wherein said electrically actuatable means is in the form of an electrically actuated solenoid having a plunger, said solenoid being provided with means for retaining said plunger in said solenoid.

3. A device as in claim 2 together with a power supply connected to said means for supplying electrical energy to the solenoid and control means connected to the power supply for adjusting the amount of energy supplied to the solenoid to adjust the impact provided by the rounded tip.

4. A device as in claim 1 wherein the flexible elongate tubular member is in the form of a catheter, an inflatable balloon mounted on the distal extremity of the catheter and means carried by the catheter for inflating and deflating the balloon.

5. A device as in claim 1 wherein said means for connecting the electrically actuatable means to the rounded tip includes a flexible elongate element.

6. A device as in claim 5 wherein said flexible elongate element is in the form of a shape-memory alloy element, electrical means connected to the shape-memory alloy element for supplying current to the shape-memory alloy element to increase the stiffness of the shape memory alloy element.

7. A device as in claim 5 further comprising a flexible coil spring having proximal and distal extremities, means securing the proximal extremity of the coil spring to the distal extremity of the flexible elongate tubular member and means securing the distal extremity of the coil spring to the rounded tip.

8. A device as in claim 7 together with a tube disposed within the spring and having a bore therein through which the flexible elongate element extends and serving to minimize the friction encountered by the flexible elongate element as it is vibrated by the electrically actuatable means.

9. A device as in claim 7 together with a plurality of circumferentially disposed flexible elongate elements having a negative coefficient of expansion disposed within the interior of the coil spring and having distal extremities secured to the distal extremity of the coil spring and conductive means for supplying energy in the form of electrical currents to the plurality of circumferentially disposed flexible elongate elements having a negative coefficient of expansion and control means for adjusting the electrical currents supplied to the plurality of circumferentially disposed flexible elongate elements having a negative coefficient of expansion to cause steering of the distal extremity of the coil spring.

10. A method for crossing a stenosis of a totally or almost totally occluded vessel of a patient by the use of a flexible elongate device having proximal and distal extremities, a rounded tip and electrically actuatable means carried by the distal extremity and connected to the rounded tip for imparting vibratory motion to the rounded tip, comprising advancing the rounded tip of the device in the vessel into contact with the stenosis and supplying electrical energy from the proximal extremity to the electrically actuatable means at the distal extremity thus generating vibratory motion at the distal extremity which imparts vibratory impact motion to the rounded tip to facilitate advancement of the rounded tip through the stenosis thereby forming a passage through the stenosis without danger of penetrating the wall of the vessel.

11. The method as in claim 10 wherein said device is a guide wire together with a balloon dilatation catheter having a balloon, further comprising the steps of inserting the balloon dilatation catheter over the guide wire to advance the balloon of the balloon dilatation catheter into and through the stenosis and inflating and deflating the balloon to enlarge the passage through the stenosis and thereafter withdrawing the balloon dilatation catheter and the guide wire.

12. A method as in claim 10 wherein said device is in the form of a balloon dilatation catheter having a balloon, further comprising the steps of advancing the balloon dilatation catheter into the passage in the stenosis after the tip has crossed the stenosis so that the balloon is in registration with the stenosis and inflating and deflating the balloon to increase the size of the passage through the stenosis and thereafter withdrawing the balloon dilatation catheter.

13. A method as in claim 8 wherein the vibratory motion is imparted in a direction which is generally parallel to the vessel wall.

14. A method as in claim 10 wherein said supplying step includes supplying electrical energy from the proximal extremity of the flexible elongate device to the electrically actuatable means at the distal extremity thus generating vibratory motion at the distal extremity of the flexible elongate device which imparts vibratory impact motion of at least 10 Hz to the rounded tip.

* * * * *